US011066671B2

(12) United States Patent
Coultas et al.

(10) Patent No.: US 11,066,671 B2
(45) Date of Patent: Jul. 20, 2021

(54) USE OF THERAPEUTIC AGENTS

(71) Applicant: THE WALTER AND ELIZA HALL INSTITUTE OF MEDICAL RESEARCH, Melbourne (AU)

(72) Inventors: Leigh Coultas, Melbourne (AU); Grant Dewson, Melbourne (AU); Emma Watson, Melbourne (AU)

(73) Assignee: The Walter and Eliza Hall Institute of Medical Research, Victoria (AU)

( * ) Notice: Subject to any disclaimer, the term of this patent is extended or adjusted under 35 U.S.C. 154(b) by 0 days.

(21) Appl. No.: 16/681,416

(22) Filed: Nov. 12, 2019

(65) Prior Publication Data

US 2020/0157539 A1 May 21, 2020

Related U.S. Application Data

(63) Continuation of application No. 15/522,600, filed as application No. PCT/AU2015/050662 on Oct. 26, 2015, now abandoned.

(30) Foreign Application Priority Data

Oct. 29, 2014 (AU) ................. 2014904330

(51) Int. Cl.
| | |
|---|---|
| *C12N 15/113* | (2010.01) |
| *A61K 38/00* | (2006.01) |
| *A61K 31/7088* | (2006.01) |
| *A61K 31/7105* | (2006.01) |
| *A61K 31/713* | (2006.01) |
| *A61P 27/02* | (2006.01) |
| *A61K 9/00* | (2006.01) |

(52) U.S. Cl.
CPC .......... *C12N 15/113* (2013.01); *A61K 9/0048* (2013.01); *A61K 31/7088* (2013.01); *A61K 31/713* (2013.01); *A61K 31/7105* (2013.01); *A61K 38/00* (2013.01); *A61P 27/02* (2018.01); *C12N 2310/14* (2013.01)

(58) Field of Classification Search
CPC ............................. C12N 15/113; A61K 38/00
See application file for complete search history.

(56) References Cited

U.S. PATENT DOCUMENTS

| 8,686,110 B2 * | 4/2014 | Colman ................. C07K 14/47 530/300 |
| 2009/0048164 A1 * | 2/2009 | Colman ................. C07K 14/47 514/1.1 |
| 2011/0160282 A1 | 6/2011 | Oh et al. |
| 2013/0035304 A1 * | 2/2013 | Walensky ............... A61P 31/00 514/35 |
| 2014/0377285 A1 * | 12/2014 | Liu ..................... A61K 31/519 424/174.1 |
| 2015/0175623 A1 | 6/2015 | Kotschy et al. |

FOREIGN PATENT DOCUMENTS

| WO | 2006/135985 A1 | 12/2006 | |
| WO | 2007/008627 A2 | 1/2007 | |
| WO | 2008/130970 A1 | 10/2008 | |
| WO | 2008/131000 A2 | 10/2008 | |
| WO | 2011/094708 A2 | 8/2011 | |
| WO | WO 2013/070976 * | 5/2013 | .......... C07D 487/00 |
| WO | 2015/097123 A1 | 7/2015 | |

OTHER PUBLICATIONS

Lirdprapmongkol et al., 2013, Chrysin overcomes TRAIL resistance of cancer cells through Mcl-1 downregulation by inhibiting STAT3 phosphorylation, International Journal of Oncology, 43: 329-337.*
Polier et al., 2011, Wogonin and related natural flavones are inhibitors of CDK9 that induce apoptosis in cancer cells by transcriptional suppression of Mcl-1, Cell Death and Disease, 2: e182 (10 pages).*
Gauthier, A. et al., "The Role of Sorafenib in the Treatment of Advanced Hepatocellular Carcinoma: An Update", 2013, Hepatology Research, vol. 43, No. 2, pp. 147-154.
Pal, H.C. et al., "Delphinidin Reduces Cell Proliferation and Induces Apoptosis of Non-Small-Cell Lung Cancer Cells by Targeting EGFR/VEGFR2 Signaling Pathways", 2013, PLOS ONE, vol. 8, No. 10, e77270.
Grossniklaus, H.E. et al., "Animal Models of Chorodial and Retinal Neovascularization", 2010, Prog Retin Eye Res., 29(6), pp. 500-519.
Stahl, A. et al., "The Mouse Retina as an Angiogenesis Model", 2010, Investigative Ophthalmology & Visual Science, vol. 51, No. 6, pp. 2813-2826.
Smith, L.E.H. et al., "Oxygen-Induced Retinopathy in the Mouse", 1994, Investigative Ophthalmology & Visual Science, vol. 35. No. 1, pp. 101-111.
Sattler M. et al., Structure of Bcl-xL-Bak Peptide Complex: Recognition Between Regulators of Apoptosis, 1997, Science, vol. 275, pp. 983-986.
Lin, X. et al., "'Seed' analysis of off-target siRNAs reveals an essential role of Mc1-1 in resistance to the small-molecule Bcl-2/Bcl-XL inhibitor ABT-737", 2006, Oncogene, vol. 26, pp. 2972-2979.
Fletcher, Steven (2019) "MCL-1 inhibitors—where are we now (2019)?", Expert Opinion on Therapeutic Patents, 29:11, 909-919, DOI: 10.1080/13543776.2019.1672661.
Xiang, W. et al., "MCL-1 inhibition in cancer treatment", OncoTargets and Therapy, Nov. 2018, 7301-7314.
Lijia Chen & Steven Fletcher (2017) Mcl-1 inhibitors: a patent review, Expert Opinion on Therapeutic Patents, 27:2, 163-178, DOI: 10.1080/13543776.2017.1249848.

* cited by examiner

*Primary Examiner* — Amber D Steele
(74) *Attorney, Agent, or Firm* — Hoffmann & Baron LLP

(57) ABSTRACT

The specification relates to the use of Mcl-1 inhibitors to promote apoptosis in vascular endothelial cells undergoing neovascularisation in disease states.

6 Claims, 12 Drawing Sheets

Specification includes a Sequence Listing.

USE OF THERAPEUTIC AGENTS

CROSS REFERENCE TO RELATED APPLICATIONS

The present application is a Continuation of co-pending National Stage application Ser. No. 15/522,600, filed Apr. 27, 2017, which claims priority from PCT Application No. PCT/AU2015/050662, filed Oct. 26, 2015, which in turn claims priority from Australian Application No. 2014904330, filed Oct. 29, 2014. Applicants claim the benefits of 35 U.S.C. § 120 as to the National Stage Application and the PCT application and priority under 35 U.S.C. § 119 as to the said Australian application, and the entire disclosures of all applications are incorporated herein by reference in their entireties.

FIELD

The specification relates generally to the field of therapeutic agents. More particularly, the specification relates to methods for modulating angiogenesis employing therapeutic agents.

BACKGROUND

Bibliographic details of references in the subject specification are also listed at the end of the specification.

Reference to any prior art in this specification is not, and should not be taken as, acknowledgement or any form of suggestion that this prior art forms part of the common general knowledge in any country.

The blood vessel network is the conduit by which nutrients and hormonal signals are distributed throughout the body. As animals grow, blood vessel networks must expand to meet the metabolic demands of the growing organs and tissues they service. To achieve this, vascular endothelial cells lining pre-existing vessels undergo a coordinated series of proliferation, differentiation, maturation and rearrangement events to generate new, functional blood vessels. This collection of morphological changes is termed angiogenesis. Angiogenesis is principally active in growing tissues, thus primarily occurs during the foetal stage of life and but for a few exceptions, is largely absent from adults. In response to pro-angiogenic stimuli, endothelial cells can be roused from dormancy to resume an angiogenic state. Inappropriate activation of angiogenesis can occur under pathological conditions, where it is often referred to as 'neovascularisation'. Neovascularisation can cause or contribute to a range of disease states, examples of which include cancer, chronic inflammatory conditions, and neovascular eye diseases such as age related macular degeneration, diabetic retinopathy, and retinopathy of prematurity.

Apoptosis, or programmed cell death, is a genetically encoded means by which redundant and potentially harmful cells are eliminated from the body. Two pathways sense and transduce apoptotic signals: the intrinsic, BCL2 family-dependent pathway and the extrinsic, death receptor-dependent pathway. The BCL2 family of cell death regulators consists of both pro-survival and pro-apoptotic members. Apoptotic stimuli including cellular stresses such as growth factor withdrawal, loss of contact with support matrices ('anoikis') and DNA damage, activate the 'BH3-only' sub-class of pro-apoptotic proteins (BAD, BID, BIK, BIM, BMF, HRK, noxa and PUMA), which then suppress the pro-survival members of the family (BCL2, BCLX, BCLW, MCL1 and A1) and activate BAK and BAX. Once unleashed, BAK and BAX cause the release of apoptogenic factors, such as cytochrome C, from mitochondria, ultimately resulting in the activation of caspase proteases that cleave vital cellular constituents and activate DNases thereby demolishing the cell.

Inhibitors with selective affinity for distinct pro-survival Bcl-2 proteins have been developed and shown to trigger the activation of the apoptotic response in specific cell types.

There is a need in the art to identify protocols for modulating angiogenesis while maintaining healthy physiological function of adult endothelial cells and tissues.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein the singular forms "a", "an" and "the" include plural aspects unless the context clearly dictates otherwise. Thus, for example, reference to "a composition" includes a single composition, as well as two or more compositions; reference to "an agent" includes one agent, as well as two or more agents; reference to "the disclosure" includes single and multiple aspects of the disclosure and so forth.

Using a genetic approach, the pro-survival protein, Mcl-1 has been shown herein to be critical for the survival of angiogenic, but not non-angiogenic (quiescent) endothelial cells of the retina. The specification enables the use of Mcl-1 inhibitors to promote apoptosis in endothelial cells undergoing angiogenesis, and therefore diminish pathologic angiogenic vasculature. In particular, the specification enables the use of Mcl-1 inhibitors to promote apoptosis in vascular endothelial cells undergoing neovascularisation in disease states, particularly that of neovascular eye disease.

As determined herein non-angiogenic (quiescent) retinal endothelial cells, such as those that make up the arteries and veins (vasculature) of the healthy adult retina are resistant to apoptosis induced by loss of Mcl-1 and angiogenic retinal endothelial cells are selectively sensitive to apoptosis induced by loss of Mcl-1. Thus, in one embodiment, the presence or distribution of disease associated angiogenic retinal endothelial cells may be selectively reduced by loss of Mcl-1 polypeptide activity.

In one embodiment, the specification provides a method of reducing pathological neovascularization in a subject. In an embodiment, the method comprises administering to a subject in need thereof an agent that suppresses Mcl-1 expression or Mcl-1 polypeptide activity. In one embodiment, the agent thereby reduces the number of angiogenic endothelial cells while substantially sparing quiescent endothelial cells in the subject.

In one embodiment, the specification enables a method of reducing pathological ocular neovascularization in a subject, the method comprising administering to a subject in need thereof an effective amount of an agent that suppresses Mcl-1 expression or Mcl-1 polypeptide activity and wherein the agent thereby reduces the number of angiogenic endothelial cells while substantially sparing quiescent endothelial cells in the eye.

Various diseases and conditions are associated with ocular neovascularization as is known to the skilled person. Diseases or conditions of the human eye and animal models thereof are described in, for example Miller et al *Opthal-* mology, 120 (1), 2013, and Stahl et al *Invest. Opthamology & Visual Science,* 51 (6) 2010. In one embodiment, the ocular neovascularization is associated with one or more of the following: retinopathy, diabetic retinopathy, pathologic choroidal or retinal neovascularization, age-related macular degeneration, retinopathy of prematurity, ocular trauma or ischemia, surgery induced edema or neovascularization, retinal vein occlusion, Coat's disease, sickle cell retinopathy and neovascular glaucoma.

In one embodiment, the agent selectively binds to Mcl-1 polypeptide and suppresses Mcl-1 polypeptide activity.

Accordingly, in some embodiments, the agent comprises a small inhibitory molecule, or a peptide or polypeptide. In one embodiment, agents are membrane penetrating to facilitate binding to Mcl-1 nucleic acid and Mcl-1 polypeptide. Conveniently, the agents are isolated or non-naturally occurring—they may be produced synthetically or recombinantly. In one embodiment, the agent is co-administered with further active agents such as a further anti-angiogenic agent.

In another embodiment, the agent selectively binds to Mcl-1 nucleic acid and suppresses Mcl-1 expression.

Here, such agents typically comprise or encode an antisense, siRNA, shRNA, miRNA, ribozyme, DNAzyme or other nucleic acid molecule. As before, such agents are typically isolated or non-naturally occurring and are made synthetically or recombinantly. Agents may be conjugates or chimeric molecules comprising mixtures of the molecules described herein.

Suitably, the agent is in the form of a composition or kit. Pharmaceutical or physiological compositions comprising suitable carriers and kits comprising same are described herein.

In one embodiment, the agent is in the form of a pharmaceutical or physiological composition.

In some embodiments, for use in the methods described herein, the agent is in the form of a pharmaceutical or physiological composition suitable for topical or ocular administration of the agent to the eye region, such as to the retina and/or choroid.

Reference to a subject includes wherein the subject is a human.

In some embodiments, the subject has been diagnosed with a disease or condition of the eye selected from the group consisting of diabetic retinopathy, pathologic choroidal or retinal neovascularization, age-related macular degeneration, retinopathy of prematurity, ocular trauma or ischemia, surgery induced edema or neovascularization, retinal vein occlusion, Coat's disease, sickle cell retinopathy and neovascular glaucoma.

In another expression of the invention, the present specification enables the use of an agent that suppresses Mcl-1 expression or Mcl-1 polypeptide activity in, or in the manufacture of a medicament for, treating a disease or condition of the eye associated with pathological neovascularization.

As known to those of ordinary skill in the field, a disease or condition of the eye associated with pathological neovascularization is selected from the group consisting of diabetic retinopathy, pathologic choroidal or retinal neovascularization, age-related macular degeneration, retinopathy of prematurity, ocular trauma or ischemia, surgery induced edema or neovascularization, retinal vein occlusion, Coat's disease, sickle cell retinopathy and neovascular glaucoma.

As discussed herein, in one embodiment, the agent selectively binds to Mcl-1 polypeptide and suppresses Mcl-1 polypeptide activity. Illustrative agents comprise a small inhibitory molecules, peptides or polypeptides that penetrate endothelial cell membranes and suppress Mcl-1 activity. In another embodiment, the agent selectively binds to Mcl-1 nucleic acid and suppresses Mcl-1 expression. Illustrative agents include molecules comprising or encoding an antisense, siRNA, shRNA, miRNA, ribozyme, DNAzyme or other isolated or non-naturally occurring nucleic acid molecule.

Pharmaceutical or physiological compositions for use in the subject methods are described herein. In one embodiment, the composition further comprises a pharmaceutically or physiologically acceptable carrier and/or diluent.

In one embodiment, the compositions are suitable for topical or ocular administration of the agent to the eye region (retina and/or choroid).

In another expression, the description enables an agent that suppresses Mcl-1 expression or Mcl-1 polypeptide activity for use in treating a disease or condition of the eye associated with pathological neovascularization wherein the agent reduces the number of angiogenic endothelial cells while substantially sparing quiescent (that is relatively or essentially quiescent) endothelial cells in the eye. As noted, in some embodiment, the agent is a membrane-penetrating small molecule inhibitor, peptide, polypeptide or nucleic acid molecule.

In one embodiment, the agent completely suppresses Mcl-1 activity in endothelial cells.

Kits comprising the subject compositions and agents are contemplated herein.

In another aspect, the specification enables a method of reducing pathological neovascularization in a subject, the method comprising administering to the subject in need thereof an agent that suppresses Mcl-1 expression or Mcl-1 polypeptide activity and wherein the agent thereby reduces the number of angiogenic endothelial cells while substantially sparing quiescent endothelial cells in the tissue.

In one embodiment, the specification enables a method of reducing a vascular malfunction disorder in a subject, the method comprising administering to the subject in need thereof an agent that suppresses Mcl-1 expression or Mcl-1 polypeptide activity and wherein the agent thereby reduces the number of angiogenic endothelial cells while substantially sparing quiescent endothelial cells in the tissue.

In one embodiment, pathological neovascularization is associated with a vascular malfunction disorder.

In one embodiment, the vascular malfunction disorder is selected from the list consisting of arteriovenous malformation, capillary malformation, hereditary haemorrhagic telangiectasia, Sturge-Weber syndrome, cerebral cavernous malformation, venous malformation, venous malformations multiple cutaneous and mucosal, blue rubber bleb nevus syndrome, glomuvenous malformation, CLOVE syndrome, Klippel-Trenaunay-Weber syndrome, Proteus syndrome and PTEN hamartoma tumour syndrome.

In one embodiment, the specification provides a method of selectively reducing the number of angiogenic or proliferating endothelial cells while sparing quiescent endothelial cells in a subject, the method comprising administering to the subject an agent that suppresses Mcl-1 expression or Mcl-1 polypeptide activity.

In one embodiment, the subject is diagnosed with a tumour.

In another embodiment, the endothelial cells are angiogenic.

In one embodiment, the subject is diagnosed with a tumour of endothelial cell origin.

As known to those of ordinary skill, the tumour of endothelial origin is selected from the group comprising capillary hemangioma, synovial hemangioma, venous hemangioma, arteriovenous hemangioma, epithelioid hemangioma, Kaposiform hemangioendothelioma, retiform hemangioendothelioma, papillary intralymphatic angioendothelioma, composite angioendothelioma, pseudomyogenic (epithelioid sarcoma-like) angioendothelioma, Kaposi sarcoma, epithelioid hemangioendothelioma, and angiosarcoma.

In one embodiment, the tumour does not over express Mcl-1.

As discussed herein, in one embodiment, the agent binds to Mcl-1 polypeptide and suppresses Mcl-1 polypeptide activity.

Illustrative agents comprise small inhibitory molecules, antibody-based, peptides (such as liner, monocyclic or bicyclic, stapled or structurally constrained peptides as known in the art) or polypeptides that penetrate endothelial cell membranes and suppress Mcl-1 activity.

In another embodiment, the agent selectively binds to Mcl-1 nucleic acid and suppresses Mcl-1 expression.

In one embodiment, apoptosis is increased in venous and sprouting regions comprising proliferating (angiogenic) vascular endothelial cells.

In one embodiment, apoptosis is not substantially increased in non-angiogenic vascular endothelial cells (spared cells).

Illustrative agents include molecules comprising or encoding an antisense, siRNA, shRNA, miRNA, ribozyme, DNAzyme or other isolated or non-naturally occurring nucleic acid molecule.

Pharmaceutical or physiological compositions for use in the subject methods are described herein and known in the art.

In some embodiments, suppression of Mcl-1 activity includes at least 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, 97%, 98%, or 99% or 100% proportionately less activity in a treated cell compared to a suitable control, or at least 1.5 fold, 2-fold, 3-fold, 4-fold, 5-fold, 6-fold, 10-fold, 20-fold, 50-fold, 100-fold, 150-fold, 1000-fold, or 10000-fold or more suppression in a treated cell compared to a suitable control.

In some embodiments, Mcl-1 polypeptide suppression by a small molecule, peptidomimetic or constrained peptide agent is selective so that the agent binds Mcl-1 polypeptide with an affinity at least 1.5 fold, 2-fold, 3-fold, 4-fold, 5-fold, 6-fold, 10-fold, 20-fold, 50-fold, 100-fold, 150-fold, 1000, or 10000-fold or more than the affinity of the agent for non-Mcl-1 domains, or non-Mcl-1 Bcl-2 polypeptides (such as Bcl-2, Bcl-XL, Bcl-W and A1). The present methods and uses are suitable for use with any suitable Mcl-1 suppressor (antagonist).

The role of Mcl-1 in protecting some tumour cells from undergoing apoptosis has fueled efforts to identify Mcl-1 inhibitors and high affinity antagonists have been identified. Illustrative Mcl-1 inhibitors comprise Mcl-1 BH3 domains (see Sattler et al Science 275, 983-986, 1997), small interfering RNAs (Lin et al., Oncogene 26: 2972, 2007). 101 See WO 2008/131000 in the name of Abbott Laboratories for 7-substituted Indole Mcl-1 inhibitors. See WO 2008/130970 in the name of Abbott Laboratories for 7-nonsubstituted Indole Mcl-1 inhibitors. See WO2015097123 and US2015175623 in the name of Servier Laboratories and Vernalis R&D Ltd for thienopyrimidine derivatives which are Mcl-1 inhibitors and where methods for their production are also described.

See also WO 2006/135985 describes BH3-only protein derived from human Bim that selectively target Mcl-1, as shown with mouse Mcl-1 as the target. Table 4a of WO 2006/135985 shows Bim BH3 peptide mutations showing Mcl-1 selectivity over other Bcl2 family members, e.g., A9E, L12A, G16E, and D17A. Example 4, last paragraph describes mutants of Bim BH3 which are specific for Mcl-1 and Table 6 shows that the double mutation of L12A & F19A in the Bim BH3 domain sequence renders that peptide selective for Mcl-1. See also WO 2007008627 describing apoptosis promoters in the name of Abbott Laboratories, see also Bajwa Expert Opin. Ther. Pat. 22, 37-55, 2012.

Any embodiment herein shall be taken to apply mutatis mutandis to any other embodiment unless specifically stated otherwise.

The above summary is not and should not be seen in any way as an exhaustive recitation of all embodiments of the present disclosure.

BRIEF DESCRIPTION OF THE FIGURES

(FIG. 1A) Representative images of retinas from 5 day old control and Mcl1 deficient (Mcl1$^{EC/EC}$) neonates stained for the vascular basement membrane protein collagen IV. Circles demarcate the boundary between the sprouting zone (external) and remodelling zone (internal). Scale bar=500 μm. (FIG. 1B) Quantification of total vascular area in 5 day old littermate control (black bar, n=3) and Mcl1$^{EC/EC}$ (grey bar, n=6) neonate retinas. (FIG. 1C) Total apoptotic (active caspase 3+) endothelial cells per mm² of total vascular area in 5 day old control (black bar, n=3) and Mcl1$^{EC/EC}$ (grey bar, n=6) neonates. (FIG. 1D) Number of apoptotic (active caspase 3+) endothelial cells associated with remodelling arteries in 5 day old Mcl1$^{EC/EC}$ (grey bar, n=6) neonates, presented as fold-change relative to control (black bar, n=3) and normalised to vascular area in the remodelling zone. (FIG. 1E) Number of apoptotic (active caspase 3+) endothelial cells associated with remodelling veins in 5 day old Mcl1$^{EC/EC}$ (grey bar, n=6) neonates, presented as fold-change relative to control (black bar, n=3) and normalised to vascular area in the remodelling zone. (FIG. 1F) Number of apoptotic (active caspase 3+) endothelial cells in the sprouting zone of 5 day old Mcl1$^{EC/EC}$ (grey bar, n=6) neonates, presented as fold-change relative to control (black bar, n=3) and normalised to vascular area in the sprouting zone. All data are presented as mean±SEM. ns=not significant, * p<0.05,  p<0.01, * p<0.001, Student's two tailed t-test.

(FIG. 2A) Representative images of arterial vasculature from control and Mcl1$^{EC/EC}$ retinas stained for the endothelial marker PECAM1. Scale bar=200 μm. (FIG. 2B) Quantification of total vascular area around arteries of control (black bar, n=3) and Mcl1$^{EC/EC}$ (grey bar, n=3) adult retinas. All three layers of adult retinal vasculature were quantified individually. Data shown are the sum of the three layers, presented relative to the total area analysed. (FIG. 2C) Representative images of venous vasculature from control and Mcl1$^{EC/EC}$ retinas stained for PECAM1. Scale bar=200 μm. (FIG. 2D) Quantification of total vascular area around veins of control (black bar, n=3) and Mcl1$^{EC/EC}$ (grey bar, n=4) adult retinas. All three layers of adult retinal vasculature were quantified individually. Data shown are the sum of the three layers, presented relative to the total area analysed.

(FIG. 2E) Number of apoptotic (active caspase $3^+$) endothelial cells per retina in control (black bar, n=2) and $Mcl1^{EC/EC}$ (grey bar, n=3) adult mice. All data are presented as mean±SEM. ns=not significant, Student's two tailed t-test.

Figure 1A:
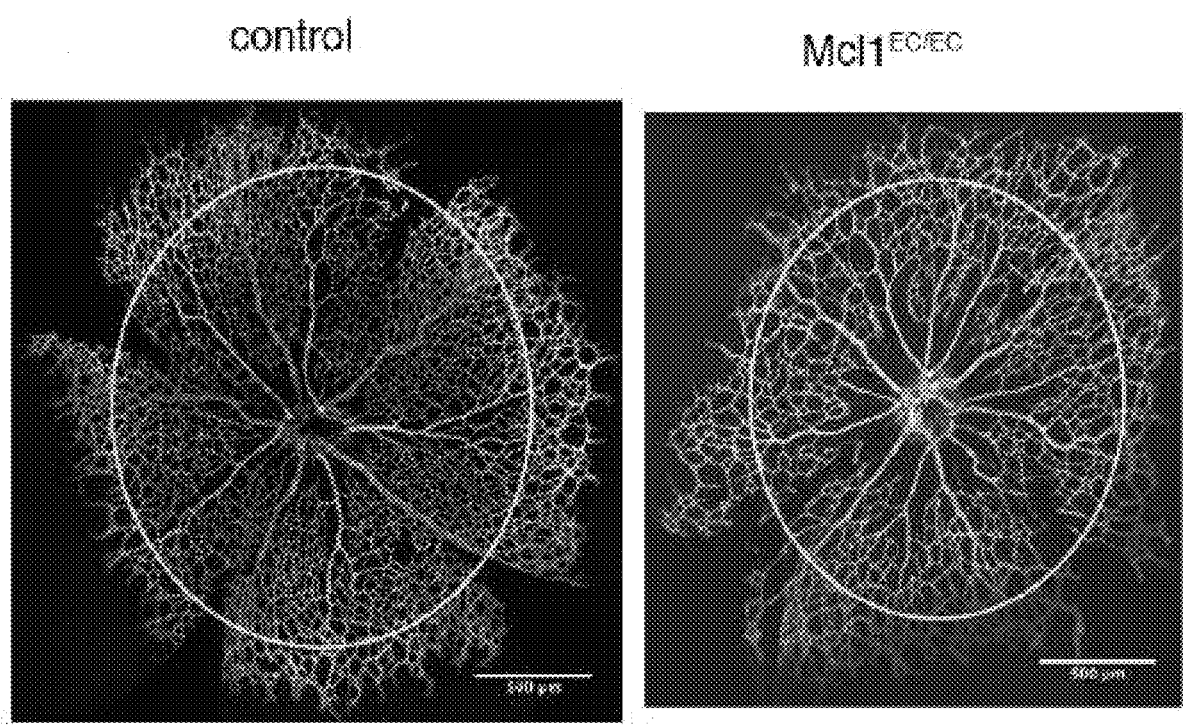
FIG. 1A-1F. Reduced vascular density and increased apoptosis in Mcl1 deficient, angiogenic retinal blood vessels.
Figure 1B:
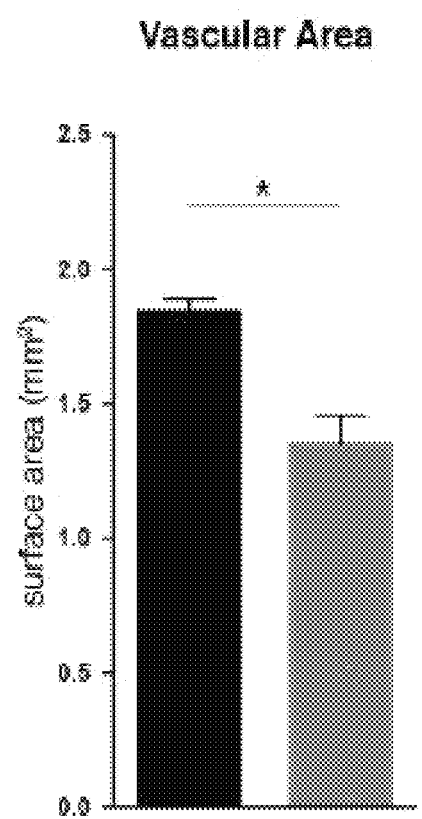

$Mcl1^{EC/+}$ and littermate controls were exposed to 75% oxygen continuously between postnatal days 7-12, then returned to room air. Neovascular area in the retina was quantified on postnatal day 17. Neovascular area in control genotype animals (control, n=5) is normalised to 100%. Neovascular area in $Mcl1^{EC/+}$ mice (n=7) is displayed as a percentage of that in littermate controls. Data are presented as mean±SEM. ** p<0.01, Student's two-tailed t-test.

DETAILED DISCUSSION OF EMBODIMENTS

The subject disclosure is not limited to particular procedures or agents, specific formulations of agents and various medical methodologies, as such may vary.

In one embodiment, the specification provides a method of reducing ocular neovascularization in a subject. In an embodiment, the method comprises administering to a subject in need thereof an agent that suppresses Mcl-1 expression or Mcl-1 polypeptide activity. In one embodiment, the agent thereby reduces the number of angiogenic endothelial cells while substantially sparing quiescent (non-angiogenic) endothelial cells in the eye.

Neovascularisation refers to the pathologic production of new blood vessels and is associated with a range of diseases and conditions known to the skilled addressee. It is caused by the inappropriate activation of angiogenesis by pro-angiogenic stimuli which stimulate otherwise non-replicating or non-angiogenic endothelial cells (referred to herein as quiescent cells) to undergo a series of proliferative, differentiation, maturation and rearrangement events to generate new functional blood vessels, typically from existing blood vessels.

The term "angiogenic" or "angiogenesis" refers to the expansion of existing blood vessel beds. Angiogenesis takes place during development, wound healing and in certain pathological conditions including those described herein.

Reference herein to "endothelial" cells refers in one embodiment to vascular endothelia i.e., essentially to the monolayer of cells lining blood vessels that are important for modulating vascular function, growth, stability (along with mural cells) and permeability. As known to those of ordinary skill, tumours of endothelial origin are selected from the group comprising capillary hemangioma, synovial hemangioma, venous hemangioma, arteriovenous hemangioma, epithelioid hemangioma, Kaposiform hemangioendothelioma, retiform hemangioendothelioma, papillary intralymphatic angioendothelioma, composite angioendothelioma, pseudomyogenic (epithelioid sarcoma-like) angioendothelioma, Kaposi sarcoma, epithelioid hemangioendothelioma, and angiosarcoma.

In one embodiment, endothelial cell are vascular endothelial cells.

Reference to "tumour" or "tumor" includes all neoplastic cell growth and proliferation, whether malignant or benign and all pre-cancerous and cancerous cells and tissues. Cancer, of course, refers to physiological condition in mammals associated with unregulated growth.

In one embodiment, "quiescent" cells are mature cells that are not undertaking a program of regulated or unregulated growth. As such, they are likely to be terminally differentiated and have cell surface markers associated with down regulated growth. In one embodiment, quiescent endothelial cells are associated with mature vasculature that is not undergoing vascular growth and angiogenesis. Vascular growth is associated with growth of new vessels, pruning of new vessels and a maturation process. As such, angiogenesis and active (non-quiescent) endothelial cells are associated with increased levels of proliferation and apoptosis. Levels of apoptosis may be determined by the skilled person, such as by determining the number of caspase $3^+$ cells.

Vascular growth includes early angiogenic sprouting of vessels and more differentiated growth of arteries and veins.

In one embodiment, growing veins and sprouting regions of the neonatal vascular bed are particularly sensitive to Mcl-1 blocking. Thus, in one embodiment, Mcl-1 inhibition provides greater inhibitory effect on venous angiogenesis.

Reference to "Mcl-1" herein includes mammalian isoforms, mutants, variants, and homologs or orthologs from various species, including without limitation murine and human forms. Mouse and human protein Mcl-1 sequences display 76% identity (82% similarity) as determined by NCBI BLAST based on the following illustrative full length sequences:

```
>Human MCL1 sequence (full length):
                                    (SEQ ID NO: 1)
MFGLKRNAVIGLNLYCGGAGLGAGSGGATRPGGRLLATEKEASARREIGG

GEAGAVIGGSAGASPPSTLTPDSRRVARPPPIGAEVPDVTATPARLLFFA

PTRRAAPLEEMEAPAADAIMSPEEELDGYEPEPLGKRPAVLPLLELVGES

GNNTSTDGSLPSTPPPAEEEEDELYRQSLEIISRYLREQATGAKDTKPMG

RSGATSRKALETLRRVGDGVQRNHETAFQGMLRKLDIKNEDDVKSLSRVM

IHVFSDGVTNWGRIVTLISFGAFVAKHLKTINQESCIEPLAESITDVLVR

TKRDWLVKQRGWDGFVEFFHVEDLEGGIRNVLLAFAGVAGVGAGLAYLIR

>Mouse MCL1 sequence (full length):
                                    (SEQ ID NO: 2)
MFGLRRNAVIGLNLYCGGASLGAGGGSPAGARLVAEEEAKARREGGGEAAL

LPGARVVARPPPVGAEDPDVTASAERRLHKSPGLLAVPPEEMAASAAAAI

VSPEEELDGCEPEAIGKRPAVLPLLERVSEAAKSSGADGSLPSTPPPPEE

EEDDLYRQSLEIISRYLREQATGSKDSKPLGEAGAAGRRALETLRRVGDG

VQRNHETAFQGMLRKLDIKNEGDVKSFSRVMVHVFKDGVTNWGRIVTLIS

FGAFVAKHLKSVNQESFIEPLAETITDVLVRTKRDWLVKQRGWDGFVEFF

HVQDLEGGIRNVLLAFAGVAGVGAGLAYLIR.
```

A biologically active variant of an Mcl-1 polypeptide may differ from that polypeptide generally by as much 100, 50 or 20 amino acid residues or suitably by as few as 1-15 amino acid residues, as few as 1-10, such as 6-10, as few as 5, as few as 4, 3, 2, or even 1 amino acid residue. Variants may be naturally occurring or produced using technology known in the art.

The agents referred to herein for use in the subject methods are Mcl-1 modulators or suppressors which change the activity of the Mcl-1 polypeptide by reducing formation of Mcl-1 or reducing the functional activity of Mcl-1 i.e., effectively suppressing apoptosis. The agents referred to herein interact or bind to an Mcl-1 nucleic acid or an Mcl-1 protein. Particular Mcl-1 inhibitors are thienopyrimidine derivatives such as those described in WO2015097123 and US2015175623 where methods for their production are also described. Preferred Mcl-1 inhibitors are highly specific for Mcl-1 such that they inhibit Mcl-1 to a greater extent than they inhibit other anti-apototic Bcl-2 family members.

Various diseases and conditions are associated with ocular neovascularization as is known to the skilled person. In one embodiment, the ocular neovascularization is associated with one or more of the following: diabetic retinopathy, pathologic choroidal or retinal neovascularization, age-related macular degeneration, retinopathy of prematurity, ocular trauma or ischemia, surgery induced edema or neovascularization, retinal vein occlusion, Coat's disease, sickle cell retinopathy and neovascular glaucoma.

In one embodiment, the agent selectively binds to Mcl-1 polypeptide and suppresses Mcl-1 polypeptide activity.

Accordingly, in some embodiments, the agent comprises a small inhibitory molecule, or a peptide or polypeptide. In one embodiment, the agents are membrane penetrating for binding to Mcl-1 nucleic acid and Mcl-1 polypeptide. Conveniently, the agents are isolated or non-naturally occurring—they may be produced synthetically or recombinantly.

Small molecules are understood to refer to chemical compounds or molecules having a molecular weight below 2000 daltons.

In another embodiment, the agent selectively binds to Mcl-1 nucleic acid and suppresses Mcl-1 expression.

Here, such agents typically comprise or encodes an antisense, siRNA, shRNA, miRNA, ribozyme, DNAzyme or other nucleic acid molecule. As before, such agents are typically isolated or non-naturally occurring and are made synthetically or recombinantly. Agents may be conjugates or chimeric molecules comprising mixtures of the molecules described herein.

Suitably, the agent is in the form of a composition or kit. Pharmaceutical or physiological composition and kits comprising same are described herein.

For use in the methods described herein, the agent is in the form of a pharmaceutical or physiological composition suitable for topical or ocular administration of the agent to the eye region, such as to the retina and/or choroid.

Reference to a subject includes wherein the subject is a human.

In some embodiments, the subject has been diagnosed with a disease or condition of the eye selected from the group consisting of diabetic retinopathy, pathologic choroidal or retinal neovascularization, age-related macular degeneration, retinopathy of prematurity, ocular trauma or ischemia, surgery induced edema or neovascularization, retinal vein occlusion, Coat's disease, sickle cell retinopathy and neovascular glaucoma.

In another expression of the invention, the present specification enables the use of an agent that suppresses Mcl-1 expression or Mcl-1 polypeptide activity in, or in the manufacture of a medicament for, treating a disease or condition of the eye associated with pathological neovascularization.

As known to those of ordinary skill in the field, a disease or condition of the eye associated with pathological neovascularization is selected from the group consisting of diabetic retinopathy, pathologic choroidal or retinal neovascularization, age-related macular degeneration, retinopathy of prematurity, ocular trauma or ischemia, surgery induced edema or neovascularization, retinal vein occlusion, Coat's disease, sickle cell retinopathy and neovascular glaucoma.

As discussed herein, in one embodiment, the agent selectively binds to Mcl-1 polypeptide and suppresses Mcl-1 polypeptide activity. Illustrative agents comprise small inhibitory molecules, peptides or polypeptides that penetrate endothelial cell membranes and suppress Mcl-1 activity. In another embodiment, the agent selectively binds to Mcl-1 nucleic acid and suppresses Mcl-1 expression. Illustrative agents include molecules comprising or encoding an antisense, siRNA, shRNA, miRNA, ribozyme, DNAzyme or other isolated or non-naturally occurring nucleic acid molecule.

Pharmaceutical or physiological compositions for use in the subject methods are described herein. In one embodiment, the composition further comprises a pharmaceutically or physiologically acceptable carrier and/or diluent.

In one embodiment, the compositions are suitable for topical or ocular administration of the agent to the eye region (particularly the retina and/or choroid).

In another expression, the description enables an agent that suppresses Mcl-1 expression or Mcl-1 polypeptide activity for use in treating a disease or condition of the eye associated with pathological neovascularization wherein the agent reduces the number of angiogenic endothelial cells while substantially sparing quiescent endothelial cells in the eye. As noted, in some embodiment, the agent is a membrane penetrating small molecule inhibitor, peptide, polypeptide or nucleic acid molecule. A reduction in the number of vascular endothelial cells can be measured in a number of different ways as would be apparent to the skilled address. Thus, the number of new blood vessels or the size of the vascular bed, or rate of growth or shrinkage of the vascular bed in a given tissue can be measured or assessed. In one embodiment, the agent completely suppresses Mcl-1 activity in vascular endothelial cells. Alternatively, or in addition the level of Mcl-1 mRNA or polypeptide may be assessed.

Kits comprising the subject compositions and agents are contemplated herein.

In another aspect, the specification enables a method of reducing pathological neovascularization in a tissue or a subject, the method comprising administering to the subject in need thereof an agent that suppresses Mcl-1 expression or Mcl-1 polypeptide activity and wherein the agent thereby reduces the number of angiogenic endothelial cells while substantially sparing quiescent endothelial cells in the tissue.

In one embodiment, the specification provides a method of selectively reducing the number of angiogenic or proliferating vascular endothelial cells while sparing quiescent endothelial cells in a subject, the method comprising administering to the subject an agent that suppresses Mcl-1 expression or Mcl-1 polypeptide activity.

In one embodiment, the subject is diagnosed with a tumour.

In another embodiment, the endothelial cells are angiogenic.

In one embodiment, the subject is diagnosed with a tumour of endothelial cell origin.

In one embodiment, the tumour of endothelial origin is selected from the group comprising capillary hemangioma, synovial hemangioma, venous hemangioma arteriovenous hemangioma, epithelioid hemangioma, Kaposiform hemangioendothelioma, retiform hemangioendothelioma, papillary intralymphatic angioendothelioma, composite angioendothelioma, pseudomyogenic (epithelioid sarcoma-like) angioendothelioma, Kaposi sarcoma, epithelioid hemangio endothelioma, and angio sarcoma.

As discussed herein, in one embodiment, the agent selectively binds to Mcl-1 polypeptide and suppresses Mcl-1 polypeptide activity.

Illustrative agents comprise a small inhibitory molecules, antibody-based, peptides (such as liner, monocyclic or bicyclic, stapled peptides as known in the art) or polypeptides that suppress Mcl-1 activity. In some embodiments, agents penetrate endothelial cell membranes. In an alternative embodiment, agents are expressed within an endothelial cell.

In another embodiment, the agent selectively binds to Mcl-1 nucleic acid and suppresses Mcl-1 expression.

Illustrative agents include molecules comprising or encoding an antisense, siRNA, shRNA, miRNA, ribozyme, DNAzyme or other isolated or non-naturally occurring nucleic acid molecule.

Pharmaceutical or physiological compositions for use in the subject methods are described herein.

In some embodiments, suppression of Mcl-1 activity includes at least 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, 97%, 98%, or 99% proportionately less activity in a treated cell compared to a suitable control, or at least 1.5 fold, 2-fold, 3-fold, 4-fold, 5-fold, 6-fold, 10-fold, 20-fold, 50-fold, 100-fold, 150-fold, 1000-fold, or 10000-fold or more suppression in a treated cell compared to a suitable control reference sample.

In some embodiments, Mcl-1 polypeptide suppression by a small molecule or peptide agent is selective so that the agent binds Mcl-1 polypeptide with an affinity at least 1.5 fold, 2-fold, 3-fold, 4-fold, 5-fold, 6-fold, 10-fold, 20-fold, 50-fold, 100-fold, 150-fold, 1000, or 10000-fold or more than the affinity of the agent for non-Mcl-1 domains, or non-Mcl-1 Bcl-2 polypeptides (such as Bcl-2, Bcl-XL, Bcl-W and A1). The present methods and uses are suitable for use with any suitable Mcl-1 antagonist.

The terms "modulate", "inhibit" or "down regulate", "suppress" and the like include antagonizing, decreasing, reducing and partially inhibiting formation, expression, level or activity of Mcl-1 in relation to reducing endothelial angiogenesis in a subject.

The subject agents are isolated or purified meaning the agents may be naturally occurring but removed from their normal physiological environment. Alternatively agents are non-naturally occurring.

In one embodiment, agents specifically bind to their target meaning they do not substantially bind other targets in a sample. In one embodiment, a first molecule specifically binds a second molecule when it binds with at least 1.5 fold, 2-fold, 3-fold, 4-fold, 5-fold, 6-fold, 10-fold, 20-fold, 50-fold, 100-fold, 150-fold, 1000-fold, or 10000-fold preference over a non-specific binding partner (e.g., BSA) or over a structurally similar protein. Ranges provided herein are understood to be a shorthand for all the values within the range.

A "reduction" or "reduces" in relation to angiogenic endothelial cells may be a reduction in vascular endothelial cells, a reduction in new blood vessels, a reduced vascular bed (area or density of blood vessels), a reduced number of veins or arteries or newly sprouted blood vessels. Reduction may be 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% relative to a suitable control. In some embodiments, reduction id 20%, 30%, 40% 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, 97%, 98%, or 99% or 100% or more, relative to a suitable control.

The term "subject" as used herein refers to an animal, in particular a mammal and more particularly a primate including a lower primate and even more particularly, a human who can benefit from the medical protocol of the present invention. A subject regardless of whether a human or non-human animal may be referred to as an individual, subject, animal, patient, host or recipient. The present invention has both human and veterinary applications. For convenience, an "animal" specifically includes livestock animals such as cattle, horses, sheep, pigs, camelids, goats and donkeys and laboratory test animals. With respect to horses, these include horses used in the racing industry as well as those used recreationally or in the livestock industry. Examples of laboratory test animals include mice, rats, rabbits, guinea pigs and hamsters. Rabbits and rodent animals, such as rats and mice, provide a convenient test system or animal model as do primates and lower primates.

As used herein, "treatment" is an approach for obtaining beneficial or desired clinical results. These include a measurable or statistically significant amelioration of the disease or condition in at least some subjects, including alleviation of symptoms, diminished extent of a disease or condition, stabilization or slowing of the disease or condition. Ideally, in relation to the eye this will include improved vision or reduced pain or a reduced rate of loss of vision, a reduced level of blindness in a subject or proportion of patients. Treatment may also refer to reduced levels of Mcl-1 polypeptide in endothelial cells leading to reduced vascularization of tumours or improved vascular re-modelling after treatment or surgery, including improved vision or a slowed rate of declining vision or stabilized vision in respect of neovascular eye disease. Such outcomes may be monitored by the attending physician.

In an illustrative embodiment, the agent is a small molecule inhibitor, a nucleic acid molecule or a protein or peptide, such as a stapled peptide or foldamer, or antibody fragment.

In one embodiment, agents that have the potential to act as suppressors include small chemical molecules, linear, monocyclic or bicyclic or constrained peptides that can penetrate a cell membrane or enter the call via an ion channel or other pore. Certain antigen binding agents derived from antibodies can display intracellular transmission, such as cartilage fish-derived antibodies (e.g. shark antibodies; see for example, Liu et al., BMC Biotechnol. 7: 78, 2007). An antigen-binding agent, or a functionally active fragment thereof, which has the capacity for intracellular transmission also includes antibodies such as camelids and llama antibodies, scFv antibodies, intrabodies or nanobodies, e.g. scFv intrabodies and VHH intrabodies. Such antigen-binding agents can be made as described by Harmsen & De Haard in Appl. Microbiol. Biotechnol. November; 77(1): 13-22, 2007; Tibary et al., Soc. Reprod. Fertil. Suppl. 64: 297-313, 2007; Muyldermans, J. Biotechnol. 74: 277 5 302, 2001; and references cited therein. In one embodiment, scFv intrabodies which are able to interfere with a protein-protein interaction are described; see for example, Visintin et al., J. Biotechnol, 135:1-15, 2008 and Visintin et al, J. Immunol. Methods, 290 (1-2): 135-53, 2008 for methods for their production. Agents may comprise a suitable cell-penetrating peptide sequence or nuclear-localizing peptide sequence such as those disclosed in Constantini et al., Cancer Biotherm. Radiopharm., 23(1): 3-24, 2008 or International Publication No. WO 2005/086800. Also useful for in vivo delivery are Vectocell or Diato peptide vectors such as those disclosed in De Coupade et al., Biochem J. 390 (pt2): 407-418, 2005 and Meyer-Losic et al., J Med Chem. 49(23): 6908-6916, 2006. Conjugates may be produced recombinantly or chemically linked or synthesised.

Small molecules, peptides etc and other agents can be screened by competitive fluorescence polarization binding assays and then progress to more selective quantitation of Mcl-1 inhibition, binding and specificity. Activity studies may be conducted using dilutions of agents and in vitro or in vivo screens for their ability to modulate endothelial angiogenesis. In vivo screens will review the ability of Mcl-1 inhibitors to modulate animal models of ocular neovascularization such as oxygen-induced neovascularisation (OIR) and laser-induced choroidal neovascularisation (LICNV). Ocular neovascularization may be associated with one or more of the following: diabetic retinopathy, pathologic choroidal or retinal neovascularization, age-related macular degeneration, retinopathy of prematurity, ocular trauma or ischemia, surgery induced edema or neovascularization, retinal vein occlusion, Coat's disease, sickle cell retinopathy and neovascular glaucoma. In addition, screens for agent effects on re-modelling, endothelial angiogenesis and tumour affected tissues and cell lines are enabled. Such screens, identified herein or known in the art are applied in vivo and used to test and develop candidate agents and determine their stability and toxicity, bioavailability etc. Thus, the term "in the manufacture of a medicament" encompasses in vitro and in vivo screening and development.

Suitable animal models of neovascular disease useful for testing agents include the oxygen induced retinopathy which employs exposure of neonates to high oxygen tension to induce loss of immature retinal vasculature (reviewed in Stahl et al (supra)). Other suitable models and screening protocols are described in Grossniklaus et al Prog. Retin. Eye Res, 29(6):500-519, 2010. Suitable models are, in particular, those that include a neovascular response such as OIR and LICNV. Natural products, combinatorial synthetic organic or inorganic compounds, fragment libraries, peptide/polypeptide/protein, nucleic acid molecules and libraries or phage or other display technology comprising these are all available to screen or test for suitable agents.

Natural products include those from coral, soil, plant, or the ocean or Antarctic environments. Libraries of small organic molecules can be generated and screened using high-throughput technologies known to those of skill in this art. See for example U.S. Pat. No. 5,763,623 and United States Application No. 20060167237. Combinatorial synthesis provides a very useful approach wherein a great many related compounds are synthesized having different substitutions of a common or subset of parent structures. Such compounds are usually non-oligomeric and may be similar in terms of their basic structure and function, for example, varying in chain length, ring size or number or substitutions. Virtual libraries are also contemplated and these may be constructed and compounds tested in silico (see for example, US Publication No. 20060040322) or by in vitro or in vivo assays known in the art. Libraries of small molecules suitable for testing are available in the art (see for example, Amezcua et al., Structure (London), 10: 1349-1361, 2002). Yeast SPLINT antibody libraries are available for testing for intrabodies which are able to disrupt protein-protein interactions (see Visintin et al., supra). Examples of suitable methods for the synthesis of molecular libraries can be found in the art. Bicyclic peptides are recently described in Liskamp Nature Chemistry 6, 855-857 2014.

Agents may be hydrocarbon-stapled peptides or miniature proteins which are alpha-helical and cell-penetrating, and are able to disrupt protein-protein interactions (see for example, Wilder et al., Chem Med Chem. 2(8): 1149-1151, 2007; & for a review see, Henchey et al., Curr. Opin. Chem. Biol., 2(6):692-697, 2008. See also U.S. Publication No. 2005/0250680.

Thus, agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is suited to peptide libraries, while the other four approaches are applicable to peptide, non-peptide oligomer or small molecule libraries of compounds. Libraries of compounds may be presented, for example, in solution, or on beads, chips, bacteria, spores and plasmids or phage as known in the art.

Nucleic acid molecules including oligonucleotides and vectors such as viruses encoding same are used to suppress gene expression of Mcl-1.

Nucleic acids (including oligonucleotides, including double or single stranded nucleic acid molecules) include DNA (gDNA, cDNA), RNA (sense RNAs, antisense RNAs, mRNAs, tRNAs, rRNAs, small interfering RNAs (SiRNAs), double-stranded RNAs (dsRNA), short hairpin RNAs (shRNAs), piwi-interacting RNAs (PiRNA), micro RNAs (miRNAs), small nucleolar RNAs (SnoRNAs), small nuclear (SnRNAs) ribozymes, aptamers, DNAzymes or other ribonuclease-type complexes are conveniently employed. Methods of producing chimeric constructs capable of inducing RNA interference in eukaryotic cells are described in the art.

The compounds in accordance with this invention preferably comprise from about 8 to about 80 nucleobases (i.e. from about 8 to about 80 linked nucleosides). One of ordinary skill in the art will appreciate that the invention embodies compounds of 8 to 80 inclusive nucleobases in length.

The sequence of the oligonucleotide or nucleic acid is designed to exhibit suitable energy related characteristics important for duplex formation, specificity, function, transport and nuclease resistance. As known in the art, sequences ideally exhibit minimal self-annealing properties, unless required. The computer program, OLIGO, may be used to estimate the behaviour of preferred antisense sequences.

RNA interference (RNAi) includes the process of gene silencing involving double stranded (sense and antisense) RNA which leads to sequence specific reduction in gene expression via target mRNA degradation. RNAi is typically mediated by short double stranded siRNAs or single stranded microRNAs (miRNA). Broadly, RNAi is initiated when a strand of RNA from either of these molecules forms a complex referred to as an RNA-induced silencing complex (RISC) which targets complementary RNA and suppresses translation. The process has been exploited for research purposes and for therapeutic application (see for example, Izquierdo et al., Cancer Gene Therapy, 12(3): 217-27, 2005) Other oligonucleotides having RNA-like properties have also been described and many more different types of RNAi may be developed. Both RNAi and antisense strategies have been used to induce stop codon suppression via inhibition of eRF1 expression (Carnes et al., RNA, 9: 648-653, 2003). Antisense oligonucleotides have been used to alter exon usage and to modulate pre-RNA splicing.

Antisense and iRNA compounds are also suitable. They may be double stranded or single stranded oligonucleotides which are RNA or RNA-like or DNA or DNA-like molecules that hybridize specifically to Mcl-1 encoding sequences. iRNA compounds are typically approximately 8 to 80 nucleobases in length and specifically hybridize to a nucleic acid region encoding Mcl-1. siRNA may have a first strand and a second strand each strand being approximately 20 to 25 nucleobases in length with the strands being complementary over at least about 19 nucleobases and having on each 3' termini of each strand a deoxythymidine dimer (dTdT) which in the double-stranded compound acts as a 3' overhang. Alternatively, the double stranded antisense compounds are blunt-ended siRNAs. Alternatively, single-stranded RNAi (ssRNAi) compounds that act via the RNAi antisense mechanism are contemplated. Further modifications can be made to the double-stranded compounds and may include conjugate groups attached to one of the termini, selected nucleobase positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double-stranded. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Nuclease insensitive antisensitive oligonucleotides are preferred as these have a substantially reduced rate of degradation by nucleases, such as RNAses and/or DNAses. As defined in this specification, oligonucleotides having modified backbones include those that retain a phosphorus atom in the backbone and those that do not have a phosphorus atom in the backbone. Modified oligonucleotides that do not have a phosphorus atom in their internucleoside backbone can also be considered to be oligonucleosides. Illustrative modified oligonucleotides include oligonucleotides such as those comprising morpholine ring (C4ON aromatic rings) in place of the natural ribose sugar moiety. Further favourable modified oligonucleotides include 2-O-methyl, PNA, LNA, morpholino or combinations of these in natural (non-modified) variants or analogs. Morpholino-based oligomeric compounds are disclosed in U.S. Pat. No. 5,034,506; WO 00024885 and WO 00045167 and are reviewed in Ekker and Landon, Genesis, 30:89-93, 2001. PNA oligonucleotides have favorable hybridization properties, high biological stability and are electrostatically neutral molecules. In PNA oligomeric compounds, the sugar-backbone of an oligonucleotide is replaced with an amide containing backbone, in particular an aminoethylglycine backbone. The nucleobases are bound directly or indirectly to an aza nitrogen atoms of the amide portion of the backbone. The preparation of PNA oligomeric compounds is disclosed for example in U.S. Pat. Nos. 5,539,082; 5,714,331; and 5,719,262. Variants including peptide nucleic acids with phosphate group (PHONA) or locked nucleic acid (LNA) or morpholino backbones or backbones with allyl linkers or amino linkers are also encompassed. Various modified oligonucleotide structures contemplated herein are described in US Patent Publication No. 2002/0125287 and U.S. Pat. No. 6,017,786 referred to herein in their entirety.

The terms "antagonist", "modifier", "compound", "active agent", "moiety", "pharmacologically active agent", "medicament", "active" and "drug" are used interchangeably herein to refer to a molecule that induces a desired pharmacological and/or physiological effect and in particular suppresses Mcl-1 activity or function or formation. This includes the active agent per se as well as pharmaceutically acceptable, pharmacologically active salts, esters, amides, prodrugs, metabolites, analogs, etc. The terms include combinations of two or more actives such as one or more inhibitors of a target activity. A "combination" also includes a two-part or more such as a multi-part pharmaceutical composition where the agents are provided separately and given or dispensed separately or admixed together prior to dispensation.

According to one embodiment, the specification provides a method of reducing neovascularization in a subject comprising the step of administering a further angiogenesis antagonist and an agent that suppresses Mcl-1 expression or Mcl-1 polypeptide activity concurrently or sequentially. According to one embodiment, the neovascularization is associated with the eye or a vascular malformation.

In one embodiment, the subject to be treated may be administered the angiogenesis antagonist initially and subsequently treated with the Mcl-1 inhibitor. In another embodiment, the subject is treated with the angiogenesis antagonist and the Mcl-1 inhibitor simultaneously. According to another embodiment, the subject is treated with the angiogenesis antagonist until the subject is unresponsive to angiogenesis antagonist treatment and then the subject is treated with an Mcl-1 inhibitor. In another embodiment, subject being treated with the Mcl-1 inhibitor has elevated the Mcl-1 RNA or protein levels in a tissue compared to tissue from a subject not suffering from the disease. In this instance, the method can further include the step of detecting Mcl-1 RNA or protein in the subject, e.g., in a diseased tissue after treatment with a further angiogenesis antagonist.

According to one embodiment, the specification provides a method of reducing neovascularization in a subject comprising the step of administering a vascular endothelial growth factor (VEGF) antagonist and an agent that suppresses Mcl-1 expression or Mcl-1 polypeptide activity concurrently (simultaneously) or sequentially. According to one embodiment, the neovascularization is associated with the eye or a vascular malformation. In one embodiment, the neovascularization is non-neoplastic. As discussed herein, antagonists may be proteins or nucleic acids, or small molecules, peptides, antibodies etc as known in the art.

In one embodiment, the subject to be treated may be administered a VEGF antagonist initially and subsequently treated with the Mcl-1 inhibitor. In another embodiment, the subject is treated with the VEGF antagonist and the Mcl-1 inhibitor simultaneously. According to another embodiment, the subject is treated with the VEGF antagonist until the subject is unresponsive to VEGF antagonist treatment and then the subject is treated with an Mcl-1 inhibitor. In another embodiment, subject being treated with the Mcl-1 inhibitor has elevated the Mcl-1 RNA or protein levels in a tissue compared to tissue from a subject not suffering from the disease. In this instance, the method can further include the step of detecting Mcl-1 RNA or protein in the subject, e.g., in a diseased tissue after treatment with a VEGF antagonist.

The term "VEGF" or "VEGF" as used herein refers to the 165-amino acid human vascular endothelial cell growth factor and related 121-, 189-, and 206-amino acid human vascular endothelial cell growth factors, as described by Leung et al. Science, 246:1306 (1989), and Houck et al. Mol. Endocrin., 5:1806 (1991), together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor.

A "VEGF antagonist" refers to a molecule capable of neutralizing, blocking, inhibiting, abrogating, reducing or interfering with VEGF activities including its binding to VEGF or one or more VEGF receptors or the nucleic acid encoding them. In one embodiment, the VEGF antagonist binds VEGF or a VEGF receptor. VEGF antagonists include anti-VEGF antibodies and antigen-binding fragments thereof, polypeptides that bind VEGF and VEGF receptors and block ligand-receptor interaction, anti-VEGF receptor antibodies and VEGF receptor antagonists such as small molecule inhibitors of the VEGFR tyrosine kinases, aptamers that bind VEGF and nucleic acids that hybridize under stringent conditions to nucleic acid sequences that encode VEGF or VEGF receptor. In one embodiment, the VEGF antagonist is selected from the group consisting of a polypeptide such as an antibody, a peptibody, an immunoadhesin, a small molecule or an aptamer. Illustrative antibodies include AVASTIN® antibody. Other examples of VEGF antagonists include: VEGF-Trap and Mucagen. An "anti-VEGF antibody" is an antibody that binds to VEGF with sufficient affinity and specificity, for example, Ranibizumab, Bevacizumab.

The subject agents are administered in an effective amount. The terms "effective amount" and "therapeutically effective amount" of an agent as used herein mean a sufficient amount of the agent to provide the desired therapeutic or physiological effect in at least a statistically significant number of subjects. Undesirable effects, e.g. side effects, are sometimes manifested along with the desired therapeutic effect. Hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

In one embodiment, an effective amount for a human subject lies in the range of about 0.1 ng/kg body weight/dose to 1 g/kg body weight/dose. In some embodiments, the range is about 1 µg to 1 g, about 1 mg to 1 g, 1 mg to 500 mg, 1 mg to 250 mg, 1 mg to 50 mg, or 1 µg to 1 mg/kg body weight/dose. Dosage regimes are adjusted to suit the exigencies of the situation and may be adjusted to produce the optimum therapeutic dose. For example, several doses may be provided daily, weekly, monthly or other appropriate time intervals. Thus, the time and conditions sufficient for reducing angiogenesis in a tissue can be determined by one skilled such as a medical practitioner who is able to specify a therapeutically or effective amount.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, amide, prodrug or derivative of a compound as provided herein is a salt, ester, amide, prodrug or derivative that this not biologically or otherwise undesirable.

For oral administration, the compounds can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, International Patent Publication No. WO 96/11698.

For parenteral administration, the compound may dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. The active agent is preferably administered in a therapeutically effective amount. The actual amount administered and the rate and time-course of administration will depend on the nature and severity of the condition being treated. Prescription of treatment, e.g. decisions on dosage, timing, etc. is within the responsibility of general practitioners or specialists and typically takes account of the disorder to be treated, the condition of the individual patient, the site of delivery, the method of administration and other factors known to practitioners. Examples of techniques and protocols can be found in Remington's Pharmaceutical Sciences, 18th Ed. Mack Publishing Company, Easton, Pa. USA, 1990. Administration may be to any tissue in need of treatment. In relation to the eye, administration is to the retina and/or choroid.

Alternatively, targeting therapies may be used to deliver the active agent more specifically to target tissues by the use of targeting systems such as antibody fragments or cell specific or cell penetrating ligands or vectors known in the art. Instead of administering these agents directly, they could be produced in the target cell, e.g. in a viral vector such as those described above or in a cell based delivery system such as described in U.S. Pat. No. 5,550,050 and International Patent Publication Nos. WO 92/19195, WO 94/25503, WO 95/01203, WO 95/05452, WO 96/02286, WO 96/02646, WO 96/40871, WO 96/40959 and WO 97/12635. The vector could be targeted to the target cells or expression of expression products could be limited to specific cells, stages of development or cell cycle stages. Cell based delivery system may be designed to be implanted in a patient's body at the desired target site and contains a coding sequence for the subject agent. Alternatively, the agent could be administered in a precursor form for conversion to the active form by an activating agent produced in, or targeted to, the cells to be treated. See, for example, European Patent Application No. 0 425 731A and International Patent Publication No. WO 90/07936. Gene therapy would be carried out according to generally accepted methods.

Delivery to the eye may be by systemic administration or by topical delivery. Intravitreal or subconjunctival delivery typically rely on use of a needle and syringe to penetrate either the wall of the eye or the conjunctival tissue to deliver aqueous agents or suspensions of agents (e.g., steroids) for acute treatment. Opthalmic formulations are prepared by formulating the compositions discussed herein as gel or semi-gel, jelly, solutions, liquids or suspensions comprising the active agent capable of being safely administered to the eye, including to the posterior portion of the eye, if required.

Diagnosis of diseases and conditions is known to those of ordinary skill in the art. Angiogenic vascular endothelial cell changes may be monitored by measuring or tracing the level of Mcl-1 mRNA or polypeptide.

Isolated endothelial cells comprising inactivated Mcl-1 are further contemplated.

The present disclosure is further described by the following non-limiting Examples.

Example 1

Figure 1C:
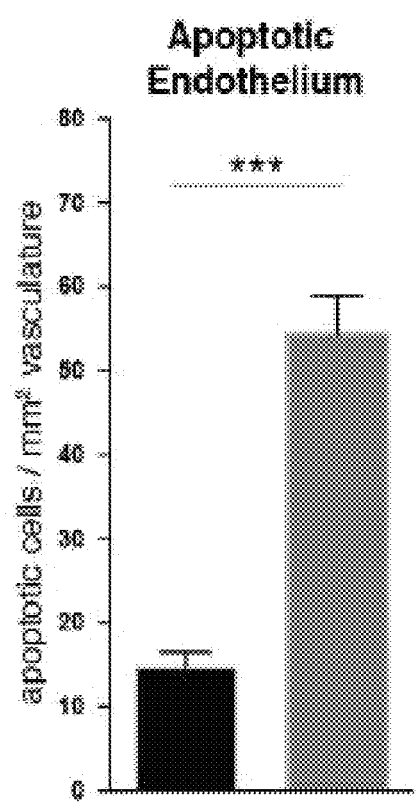

MCL1 is Required for Retinal Endothelial Cell Survival During Angiogenesis:

To demonstrate the role of MCL1 in endothelial cell survival, inducible cre/lox technology was employed to inactivate the Mcl1 gene in endothelial cells of mice in a temporally regulated manner. Mice lacking Mcl1 in endothelial cells are hereafter denoted Mcl1EC/EC. The retina initially develops as an avascular tissue. In mice, vascularisation of the retina begins at birth and is completed after approximately 21 days. To determine the role of MCL-1 in endothelial survival during angiogenesis, Mcl1EC/EC neonates were examined at postnatal day (P)5, a period when extensive angiogenesis is normally observed in the mouse retina (FIG. 1A). Total vascular area in Mcl1EC/EC retinas was significantly reduced compared to littermate controls (FIGS. 1A & B). This was accompanied by a highly significant increase in apoptotic endothelial cell death as assessed by staining for active caspase 3 (FIG. 1C).

Figure 1D:
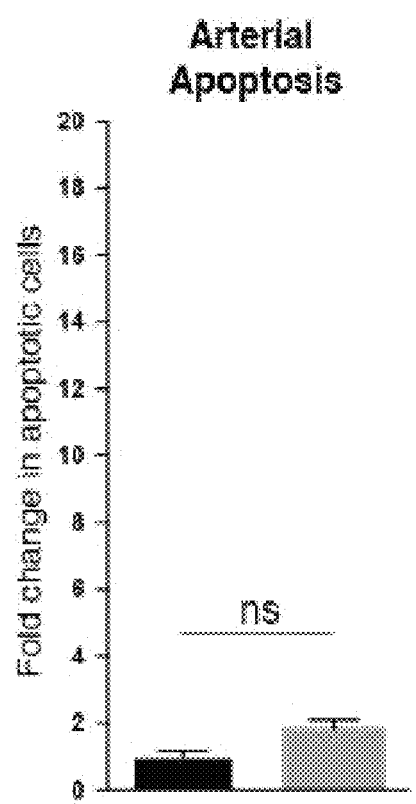
Figure 1E:
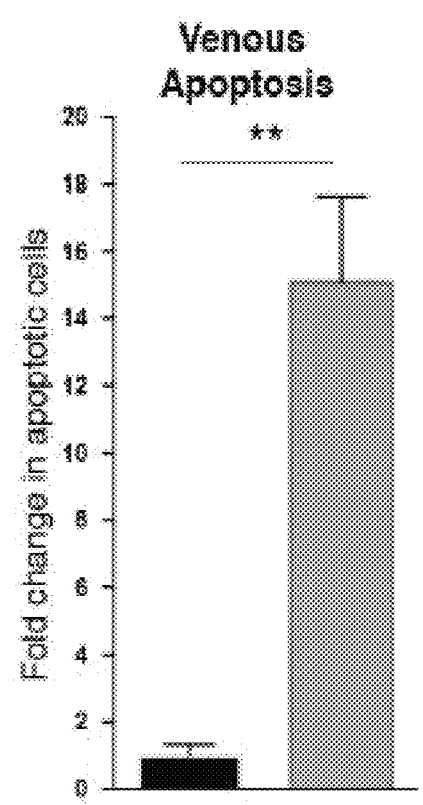
Figure 1F:
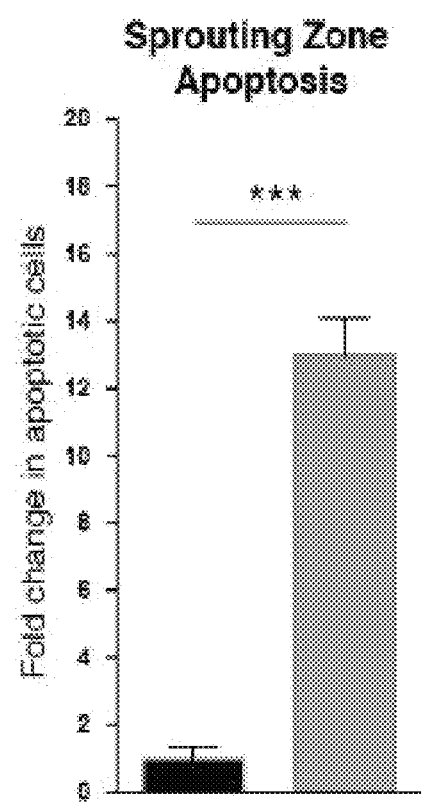

The angiogenic vasculature of the retina can be divided into two major zones: a remodelling zone (containing maturing arteries and veins), and a sprouting zone (where the majority of vascular growth occurs) (FIG. 1A). Apoptosis was slightly but not significantly elevated around arteries in the remodelling zone of Mcl1EC/EC neonatal retinas (FIG. 1D). In contrast, apoptosis was highly significantly increased (15 fold) in endothelial cells around remodelling veins (FIG. 1E). Likewise, apoptosis was highly significantly increased (13 fold) in the sprouting zone of the angiogenic vessel network (FIG. 1F).

Example 2

MCL1 is not Required for Survival of Quiescent Retinal Endothelial Cells

Figure 2A:
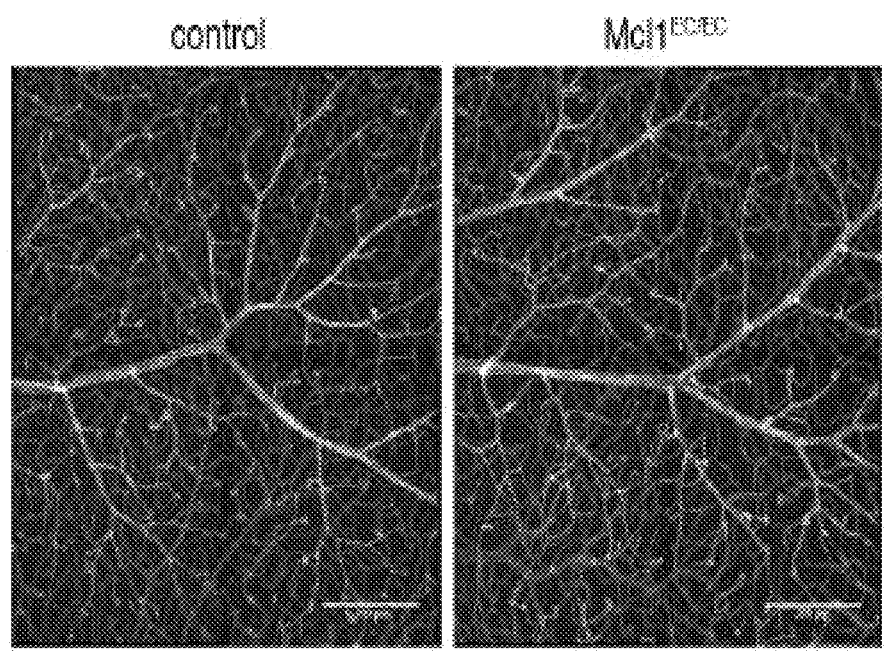
FIG. 2A-2E. MCL1 is not required for the survival of quiescent retinal vasculature.
Figure 2B:
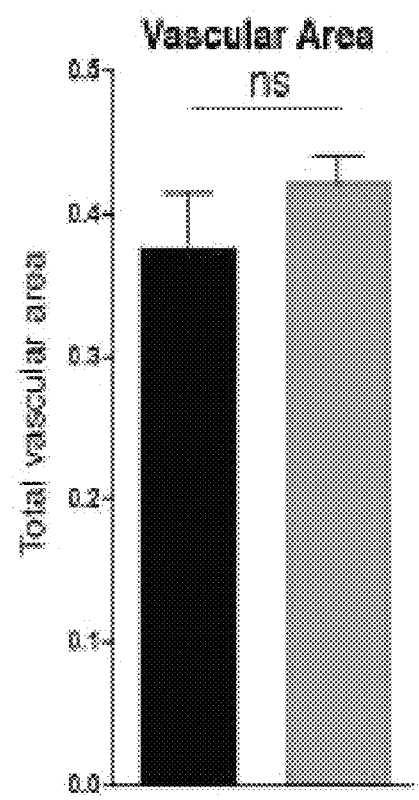
Figure 2C:
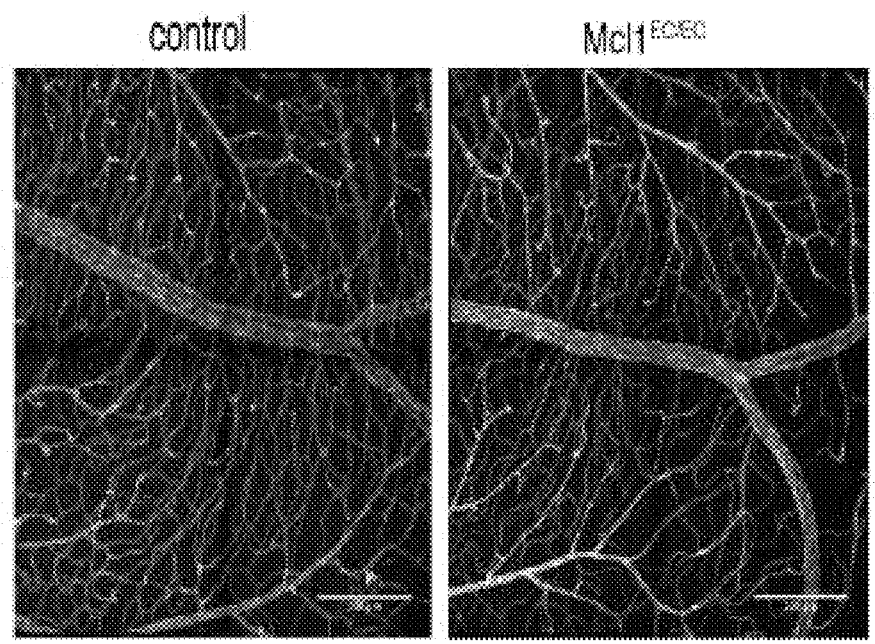
Figure 2D:
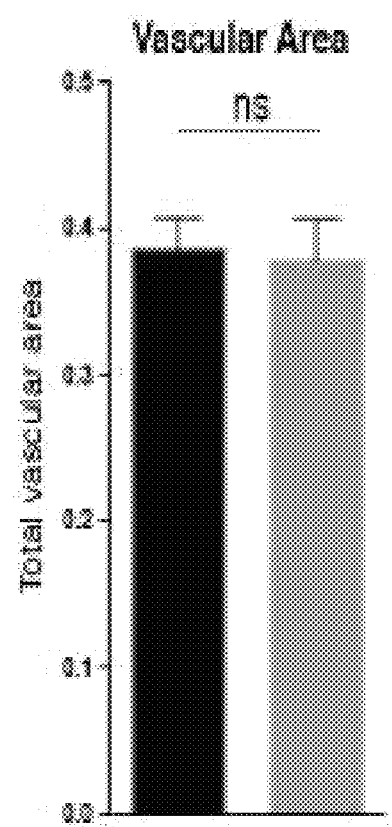
Figure 2E:
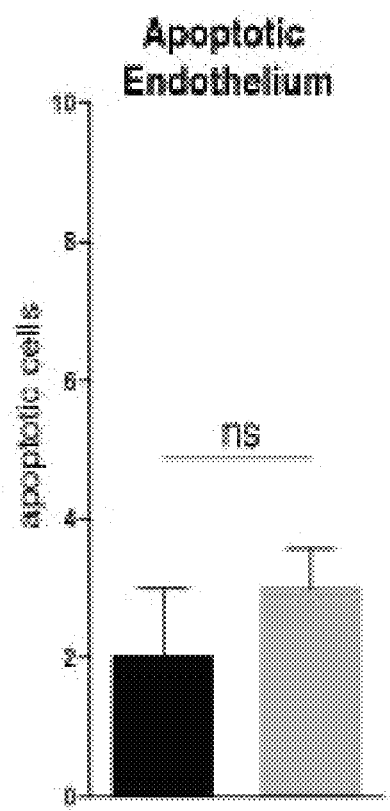

To determine the role of MCL1 in quiescent endothelial cell survival, the retinal vasculature was examined following deletion of Mcl1 from the quiescent vasculature of adult mice. The mature vasculature of the retina forms 3 distinct layers. The total vascular area (sum of all 3 layers) of control and Mcl1EC/EC retinas was determined both around arteries (FIG. 2A) and veins (FIG. 2C). There was no difference in the amount of vasculature in the vicinity of arteries (FIG. 2B) or veins (FIG. 2D) of the mutants relative to controls. Endothelial apoptosis as assessed by staining for active caspase 3, was rare in both control and Mcl1EC/EC retinas with no significant difference observed between mutants or controls (FIG. 2E).

Example 3

Loss of MCL1 Activity Prevents Pathological Neovascularisation in the Retina.

Figure 3:
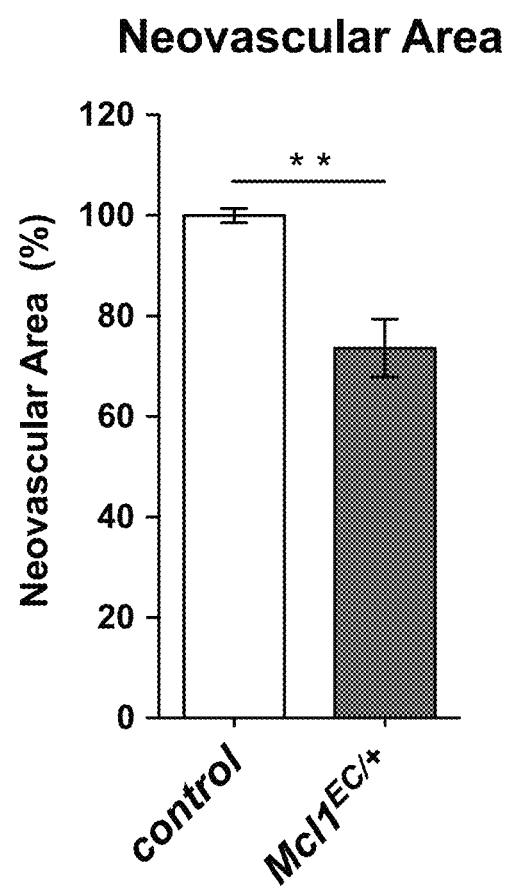
FIG. 3. Pathological neovascularisation is dependent on MCL1 activity.

The murine oxygen-induced retinopathy (OIR) procedure (Smith, 1994) replicates the pathological neovascularisation that occurs in human proliferative retinal vascular diseases such as diabetic retinopathy and retinopathy of prematurity. To determine if MCL1 was required for such pathological retinal neovascularisation, we subjected mice lacking a single copy of the Mcl1 gene in their endothelial cells (Mcl1EC/+) to the OIR procedure Smith et al., Invest Ophthalmol Vis Sci. 35 (1) 1994 Mcl1EC/+ mice were found to contain significantly less retinal neovascularisation than their control genotype littermates (FIG. 3).

These results demonstrate that MCL1 activity is required for pathological neovascularisation of the kind observed in diabetic retinopathy and oxygen-induced retinopathy. Further, they demonstrate that MCL1 is limiting in this process, as the loss of a single copy of MCL1 was sufficient to reduce pathological neovascularisation.

Many modifications will be apparent to those skilled in the art without departing from the scope of the present description.

BIBLIOGRAPHY

Amezcua et al., *Structure (London)*, 10: 1349-1361, 2002.
Ausubel et al., *Curr. Prot. in Mol. Biol.*, Supp. 47, John Wiley & Sons, N Y, 1999.
Bajwa *Expert Opin. Ther. Pat.* 22, 37-55, 2012.
Canes et al., *RNA*, 9: 648-653, 2003.
Constantini et al., *Cancer Biotherm. Radiopharm.*, 23(1): 3-24, 2008.
De Coupade et al., *Biochem J.* 390 (pt2): 407-418, 2005.
Ehling et al., *Development* 140, 3051-3061, 2013.
Ekker and Landon, *Genesis,* 30:89-93, 2001.
Grossniklaus et al., *Prog. Retin. Eye Res.* 29(6):500-519, 2010.
Harmsen & De Haard in *Appl. Microbiol. Biotechnol.* November; 77(1): 13-22, 2007.
Henchey et al., *Curr Opin Chem Biol.,* 2(6):692-697, 2008.
Liu et al., *BMC Biotechnol.* 7: 78, 2007.
Lin et al., *Oncogene* 26: 2972, 2007.
Liskamp, *Nature Chemistry* 6: 855-857, 2014.
Meyer-Losic et al., *J Med Chem.* 49(23): 6908-6916, 2006.
Miller et al., *Opthalmology* 120 (1) 2013.
Muyldermans, *J. Biotechnol.* 74: 277 5 302, 2001.
Remington's Pharmaceutical Sciences, $18^{th}$ Ed. Mack Publishing Co., Easton, Pa. USA, 1990.
Sattler et al., *Science* 275: 983-986, 1997.
Smith et al., *Invest Ophthalmol Vis Sci.* 35(1):101-11, 1994
Stahl et al., *Invest. Opthamology & Visual Science* 51 (6), 2010.
Tibary et al., *Soc. Reprod. Fertil. Suppl.* 64: 297-313, 2007.
Visintin et al., *J. Biotechnol,* 135:1-15, 2008.
Visintin et al., *J. Immunol. Methods,* 290 (1-2): 135-53, 2008.
Wilder et al., *Chem Med Chem.* 2 (8): 1149-1151, 2007.

The invention claimed is:

1. A method of reducing ocular neovascularization in a subject wherein the ocular neovascularization is pathological choroidal neovascularization or retinal neovascularization, the method comprising treating the subject with a VEGF antagonist, determining that the subject is unresponsive to the VEGF antagonist treatment, and administering to the subject an agent, wherein the agent is a small molecule inhibitor that binds to Mcl-1 polypeptide and suppresses Mcl-1 polypeptide activity, wherein the agent is highly specific for Mcl-1 verses non-Mcl-1 Bcl-2 polypeptides, wherein the agent is active in endothelial cells and suppresses Mcl-1 activity in endothelial cells and reduces the number of angiogenic vascular endothelial cells while substantially sparing quiescent vascular endothelial cells in the eye, wherein the agent is in a pharmaceutical or physiological composition and the pharmaceutical or physiological composition is administered topically to the eye region or ocularly, and wherein administering the agent is for a time and under conditions effective to reduce the formation of new blood vessels in the eye of the subject.

2. The method of claim 1, wherein the subject is a human.

3. The method of claim 1 wherein the agent is active in endothelial cells and completely suppresses Mcl-1 expression or activity in endothelial cells.

4. The method of claim 1, wherein apoptosis is increased in venous and sprouting regions comprising proliferating vascular endothelial cells.

5. The method of claim 1, wherein apoptosis is not substantially increased in non-angiogenic vascular endothelial cells.

6. The method of claim 1, wherein the subject has elevated Mcl-1 RNA or protein levels in diseased tissue compared to a subject not suffering from ocular neovascularization.

* * * * *

SEQUENCE LISTING

<160> NUMBER OF SEQ ID NOS: 2

<210> SEQ ID NO 1
<211> LENGTH: 350
<212> TYPE: PRT
<213> ORGANISM: Homo sapiens

<400> SEQUENCE: 1

Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
            20                  25                  30

Gly Arg Leu Leu Ala Thr Glu Lys Glu Ala Ser Ala Arg Arg Glu Ile
        35                  40                  45

Gly Gly Gly Glu Ala Gly Ala Val Ile Gly Gly Ser Ala Gly Ala Ser
    50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Leu Asp Gly
            115                 120                 125

Tyr Glu Pro Glu Pro Leu Gly Lys Arg Pro Ala Val Leu Pro Leu Leu
            130                 135                 140

Glu Leu Val Gly Glu Ser Gly Asn Asn Thr Ser Thr Asp Gly Ser Leu
145                 150                 155                 160

Pro Ser Thr Pro Pro Pro Ala Glu Glu Glu Glu Asp Glu Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
            195                 200                 205

Ala Leu Glu Thr Leu Arg Arg Val Gly Asp Gly Val Gln Arg Asn His
    210                 215                 220

Glu Thr Ala Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
            260                 265                 270

Phe Val Ala Lys His Leu Lys Thr Ile Asn Gln Glu Ser Cys Ile Glu
        275                 280                 285

Pro Leu Ala Glu Ser Ile Thr Asp Val Leu Val Arg Thr Lys Arg Asp
            290                 295                 300

Trp Leu Val Lys Gln Arg Gly Trp Asp Gly Phe Val Glu Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
            340                 345                 350

<210> SEQ ID NO 2
<211> LENGTH: 331

```
<212> TYPE: PRT
<213> ORGANISM: Mus musculus

<400> SEQUENCE: 2

Met Phe Gly Leu Arg Arg Asn Ala Val Ile Gly Leu Asn Leu Tyr Cys
1               5                   10                  15

Gly Gly Ala Ser Leu Gly Ala Gly Gly Ser Pro Ala Gly Ala Arg
            20                  25                  30

Leu Val Ala Glu Glu Ala Lys Ala Arg Arg Glu Gly Gly Glu Ala
            35                  40                  45

Ala Leu Leu Pro Gly Ala Arg Val Val Ala Arg Pro Pro Val Gly
    50                  55                  60

Ala Glu Asp Pro Asp Val Thr Ala Ser Ala Glu Arg Arg Leu His Lys
65                  70                  75                  80

Ser Pro Gly Leu Leu Ala Val Pro Pro Glu Glu Met Ala Ala Ser Ala
                85                  90                  95

Ala Ala Ala Ile Val Ser Pro Glu Glu Glu Leu Asp Gly Cys Glu Pro
            100                 105                 110

Glu Ala Ile Gly Lys Arg Pro Ala Val Leu Pro Leu Leu Glu Arg Val
            115                 120                 125

Ser Glu Ala Ala Lys Ser Ser Gly Ala Asp Gly Ser Leu Pro Ser Thr
    130                 135                 140

Pro Pro Pro Pro Glu Glu Glu Glu Asp Asp Leu Tyr Arg Gln Ser Leu
145                 150                 155                 160

Glu Ile Ile Ser Arg Tyr Leu Arg Glu Gln Ala Thr Gly Ser Lys Asp
                165                 170                 175

Ser Lys Pro Leu Gly Glu Ala Gly Ala Ala Gly Arg Arg Ala Leu Glu
            180                 185                 190

Thr Leu Arg Arg Val Gly Asp Gly Val Gln Arg Asn His Glu Thr Ala
        195                 200                 205

Phe Gln Gly Met Leu Arg Lys Leu Asp Ile Lys Asn Glu Gly Asp Val
    210                 215                 220

Lys Ser Phe Ser Arg Val Met Val His Val Phe Lys Asp Gly Val Thr
225                 230                 235                 240

Asn Trp Gly Arg Ile Val Thr Leu Ile Ser Phe Gly Ala Phe Val Ala
                245                 250                 255

Lys His Leu Lys Ser Val Asn Gln Glu Ser Phe Ile Glu Pro Leu Ala
            260                 265                 270

Glu Thr Ile Thr Asp Val Leu Val Arg Thr Lys Arg Asp Trp Leu Val
        275                 280                 285

Lys Gln Arg Gly Trp Asp Gly Phe Val Glu Phe Phe His Val Gln Asp
    290                 295                 300

Leu Glu Gly Gly Ile Arg Asn Val Leu Leu Ala Phe Ala Gly Val Ala
305                 310                 315                 320

Gly Val Gly Ala Gly Leu Ala Tyr Leu Ile Arg
                325                 330
```